(12) United States Patent
Rich et al.

(10) Patent No.: US 7,980,246 B2
(45) Date of Patent: Jul. 19, 2011

(54) LOW DEADSPACE AIRWAY ADAPTER

(75) Inventors: David R. Rich, Glastonbury, CT (US);
John A. Triunfo, Jr., Fairfield, CT (US);
Richard S. Tencza, Wallingford, CT (US); John L. Sandor, North Haven, CT (US)

(73) Assignee: RIC Investments, LLC, Wilmington, DE (US)

( * ) Notice: Subject to any disclaimer, the term of this patent is extended or adjusted under 35 U.S.C. 154(b) by 1475 days.

(21) Appl. No.: 11/418,852

(22) Filed: May 5, 2006

(65) Prior Publication Data

US 2006/0201517 A1 Sep. 14, 2006

Related U.S. Application Data

(63) Continuation-in-part of application No. 10/680,848, filed on Oct. 7, 2003, now Pat. No. 7,059,322.

(60) Provisional application No. 60/417,899, filed on Oct. 11, 2002.

(51) Int. Cl.
*A61M 16/00* (2006.01)
*A62B 7/02* (2006.01)
*A62B 9/04* (2006.01)

(52) U.S. Cl. .......... 128/207.14; 168/204.22; 168/202.27

(58) Field of Classification Search ............. 128/204.22, 128/207.14, 207.16, 911, 912, 202.27, 200.26, 128/200.24; 285/224–229, 235, 299, 300; 604/164.01–167.06
See application file for complete search history.

(56) References Cited

U.S. PATENT DOCUMENTS

| | | | | |
|---|---|---|---|---|
| 243,192 A | * | 6/1881 | Baylor | 285/226 |
| 603,222 A | * | 4/1898 | McLean | 285/110 |
| 3,857,588 A | * | 12/1974 | Curtin | 285/31 |
| 4,249,527 A | * | 2/1981 | Ko et al. | 128/204.18 |
| 4,531,619 A | * | 7/1985 | Eckels | 188/371 |
| 4,558,708 A | | 12/1985 | Labuda et al. | |
| 4,668,215 A | | 5/1987 | Allgood | |
| 4,805,611 A | * | 2/1989 | Hodgkins | 128/207.14 |
| 4,815,459 A | | 3/1989 | Beran | |
| 5,101,817 A | | 4/1992 | Etter | |
| 5,178,138 A | | 1/1993 | Walstrom et al. | |
| 5,213,095 A | * | 5/1993 | Dague | 128/204.18 |
| 5,433,195 A | | 7/1995 | Kee et al. | |
| 5,642,726 A | | 7/1997 | Owens et al. | |
| 5,657,750 A | | 8/1997 | Colman et al. | |
| 5,693,944 A | | 12/1997 | Rich | |
| 5,789,660 A | * | 8/1998 | Kofoed et al. | 73/23.2 |
| 5,857,461 A | | 1/1999 | Levitsky et al. | |
| 6,422,240 B1 | | 7/2002 | Levitsky et al. | |
| 6,437,316 B1 | | 8/2002 | Colman et al. | |
| 6,439,231 B1 | | 8/2002 | Fukunaga et al. | |
| 6,516,803 B1 | | 2/2003 | Enzinger | |

FOREIGN PATENT DOCUMENTS

WO WO 00/00246 A1 1/2000
WO WO 00/74756 A1 12/2000
WO WO 0074756 A1 * 12/2000

* cited by examiner

*Primary Examiner* — Justine R Yu
*Assistant Examiner* — Valerie Skorupa

(57) ABSTRACT

An airway adapter suitable for use with patients having low tidal volumes, e.g., neonates, which minimizes deadspace in the airway and promotes smooth flow of gases through the adapter. The adapter includes a first portion adapted to couple to a tubular adapter, such as an endotracheal tube adapter, and a second portion adapted to couple to a ventilation tube. A longitudinally compressible member is coupled to the first portion to minimize deadspace in the adapter. A portion of the compressible member resiliently contacts and seals against a tubular adapter upon assembly of the airway adapter therewith.

18 Claims, 8 Drawing Sheets

LOW DEADSPACE AIRWAY ADAPTER

CROSS-REFERENCE TO RELATED APPLICATIONS

This application is a Continuation-In-Part (CIP) under 35 U.S.C. §120 from U.S. patent application Ser. No. 10/680,848, filed Oct. 7, 2003, which claims priority under 35 U.S.C. §119(e) from provisional U.S. patent application No. 60/417,899 filed Oct. 11, 2002 the contents of which are incorporated herein by reference.

BACKGROUND OF THE INVENTION

1. Field of the Invention

The present invention relates generally to an airway adapter for use in connecting an endotracheal tube to a ventilation apparatus, and, in particular, to an airway adapter for use with a sidestream or mainstream gas monitoring system that minimizes deadspace in the breathing circuit so that it is especially suited for use with a patient having a small endotracheal tube, i.e., an inner diameter of less than approximately 4.0 mm, and commensurately low tidal volumes.

2. Description of the Related Art

During medical treatment, a patient's exhalations are often times monitored and analyzed to determine the gaseous composition thereof. For instance, monitoring of the carbon dioxide ($CO_2$) content of a patient's exhalations is often desirable. Typically, the $CO_2$ (or other gaseous) content of a patient's exhalations is monitored by transferring a portion, or sample, of the patient's expired gas to a suitable sensing mechanism and monitoring system.

Monitoring of exhaled gases is typically accomplished utilizing either mainstream or sidestream monitoring system. In a mainstream monitoring system, the gaseous content of a patient's exhalation is measured in-situ in the patient's airway. In a sidestream monitoring system, on the other hand, a sample of the respired gases is removed from the patient's airway and transported through a gas sampling line to a sensing mechanism located some distance from the patient for monitoring.

In sidestream monitoring systems, it is desirable for a number of reasons to minimize the volume of gas removed, i.e., sample rate, from the airway for sampling. First, the lesser the volume of gas removed from the airway, the lesser the disturbance to the patient's ventilation. This is particularly important for patients having small tidal volumes, such as neonates and infants—which have average tidal volumes equivalent to about half the average adult tidal volume. Second, as the sample gas often contains contaminants and other constituents that must be removed prior to measurement, a reduced sample size, in turn, results in a smaller volume of contaminants and other constituents that must be removed from the sample in order to achieve accurate monitoring results. Third, when respiratory assistance is given in the operating room to patients under anesthesia, the sample gas will likely contain anesthetic agents that must be safely vented. Further, such anesthetic agents are often expensive and should not be wasted. Accordingly, the smaller the gas sample, the smaller the volume of anesthetic agents wasted and that must be properly handled.

Early gas sampling systems were limited by the response time of the sensing mechanism and required sampling rates of approximately 180-200 ml/min to achieve acceptable accuracy at higher respiratory rates. Such high sampling rates are not viable for low tidal volume patients, due to the unacceptable impact of the high sampling rate on the ventilation of the patient. Fortunately, recent advances in sensing technologies have permitted sampling rates to be reduced to approximately 50 ml/min, while still achieving acceptable accuracy. With viable low rate sensing mechanisms now available, design challenges for gas sampling systems for use with low tidal volume patients have shifted to providing a system in which a sample can be extracted from the breathing circuit without introducing excessive deadspace, i.e., void volume, into the breathing circuit, adding flow resistance to the breathing circuit, and/or losing the integrity of the sample at the sampling point in the breathing circuit.

There is often a discrepancy between the cross-sectional size of an endotracheal tube and the cross-sectional size of a ventilation tube. Thus, airway adapters are generally placed between the endotracheal tube and the ventilating tube to facilitate a relatively seamless connection therebetween. An airway adapter that is directly connected to an endotracheal tube is generally referred to as an endotracheal tube adapter.

If desired, an airway adapter may also include a sampling port through which gas samples are collected and transported to a sidestream gas monitoring system for analysis. Many conventional sampling airway adapters include a small opening extending through the wall of the adapter into the gas flow path through which gas samples are collected. However, termination of the sampling port in the wall of the adapter may permit contaminants and other constituents, which tend to collect along the inner wall of the adapter, to enter the sensing mechanism. Entry of such contaminants and other constituents into the sensing mechanism is undesired, as it may lead to inaccurate monitoring results. Accordingly, sampling airway adapters have been modified to include ports that extend beyond the inner surface of the wall of the adapter and into the center of the conduit through which gases flow.

Accurate gas analysis measurements depend, in part, upon the rapid and complete exchange of gases through the airway adapter, so as to maintain the characteristics or fidelity of the parameters being measured, e.g., the waveform of the gas to be analyzed. Internal mixing of respired gases and alterations in the waveform of the gas to be analyzed reduces the accuracy of the gas measurements and, thus, may produce results which do not accurately reflect the patient's medical status. In addition, it is desirable to prevent or minimize "unswept volume" in the airway adapter. As used herein, "unswept volume refers to eddies or stagnant areas along the gas flow where the incoming gas fails to fully flush out the gas already in the airway adapter.

Airway adapters and the components to which they connect typically are manufactured as plastic injection moldings. To ensure suitably tight joints between airway adapters and the components which they connect, adapters and components are generally produced with slightly tapered portions so that one component fits tightly into the complementary component or adapter. However, there are fairly wide manufacturing tolerances for such plastic parts. As a result, loose-fitting connections will seal only when one component is pushed much farther into the other than is the case with tight-fitting connections. Consequently, the amount of deadspace produced by the connection of the components and/or airway adapters varies considerably and, for a tight-fitting pair of components, may be of considerable and undesirable magnitude, because, for example, the relatively large amount of deadspace may increase the effects of gas mixing and may result in rebreathing.

In view of this problem, airway adapters that seek to reduce the volume of deadspace introduced into the airway have been developed. Many of the proposed designs, however, are unsuitable for patients in which a very small flow is involved, e.g., neonatal patients, because even a small airway deadspace can cause significant mixing of the neonate's exhaled gases which, again, may produce inaccurate monitoring results.

One attempt to create an airway adapter suitable for neonatal patients that decreases the volume of deadspace in the airway, and purportedly maintains a smooth, laminar flow of gases, is described in PCT International Patent Application Publication WO 00/74756 to Oridion Medical, Ltd. ("hereinafter the '756 application"). FIG. 1 in the present application illustrates a first embodiment of an airway adapter 10 taught by the '756 application, and. FIG. 2 in the present invention illustrates a second embodiment of an airway adapter taught by the '756 application.

As shown in FIG. 1, adapter 10 includes a central passage 12 and a tubular insert 14 that is located inside the central passage. Insert 14 has an inside bore diameter 16 that substantially approximates the shape and size of the inside diameter of the tubular bore of the adapter 10. At the inner end of insert 14, the internal passageway opens out into a funnel shaped section 18, such that along the length of the funnel shaped section 18, internal diameter 16 of insert 14 gradually increases from the value it has along the majority of its length until it becomes equal to the internal diameter of central passage 12. A second end 20 of adapter 10 has a wide bore tubular opening 22 of a dimension suitable for connection to a standard ventilator tube. A sampling port arrangement 24 is built into the center section of airway adapter 10 to allow attachment of a gas sampling line thereto.

It can be appreciated that insert 14 can slide in a longitudinal direction, as indicated by arrows 28. However, the degree to which insert 14 extends into central passage 12 is limited by an outer end section 36 of passage 12 and a lip 34 provided on insert 14. The inward motion of the insert is arrested when lip 34 contacts end 36.

As shown in FIG. 2, the adapter includes a sleeve 38 instead of an insert, and utilizes a spring 40 to ensure positive contact between sleeve 38 and the adapter.

Sleeve 38 slides on the outside of the wall 42, which defines the central passage through the airway adapter. The funnel shaped enlargement 44 in the airway bore is incorporated into the wall 42 of the central passage, and is thus fixed in this position. The sleeve seals against the inner wall 46 of the adapter where the internal diameter increases in a stepwise fashion. A seal 47 provided at one end of sleeve 38 is maintained in positive contact with an inner wall 48 of the adapter by spring 38.

While the two airway adapter embodiments discussed in the '756 application may provide a low volume airway adapter, they may not represent an optimal solution to the problems confronting this technology. For example, the sliding spring mechanism taught by the embodiments disclosed in the '756 application may become clogged with debris rendering it inoperative. Furthermore, the adapters taught by the '756 application require multiple parts that may be costly and time consuming to assemble, especially with respect to the sliding mechanism. Accordingly, other airway adapters that minimize deadspace, promote smooth flow of gases, minimize unswept volume and that are suitable for use with low tidal volume patients would be advantageous.

BRIEF SUMMARY OF THE INVENTION

The present invention provides an airway adapter that is particularly suitable for, but not limited to, use with patients having low tidal volumes, e.g., neonates, which minimizes deadspace in the airway and unswept volume, and which promotes smooth flow of gases through the adapter.

The airway adapter according to a first embodiment of the present invention includes a substantially tubular first portion that comprises (1) a wall having a first end portion, a second end portion, and a first bore defined therein, and (2) a protrusion operatively coupled to the wall and having a second bore defined therethrough, wherein the protrusion is axially aligned with the first bore. A longitudinally compressible member is coupled to the protrusion such that a first portion of the compressible member extends beyond an end of the protrusion, wherein the first portion of the compressible member includes a third bore defined therein in communication with the second bore. A substantially tubular second portion is coupled to the first end portion of the tubular first portion. A fourth bore is defined in the second portion, and the second, third bore, and fourth bores are in fluid communication so as to define at least a portion of a gas flow path through the airway adapter. Also, a flow measuring assembly, a gas constituent monitoring assembly, or are provided in the airway adapter.

The airway adapter according to a further embodiment of the present invention includes a substantially tubular first portion comprising a wall having a first end portion, a second end portion, and a first bore defined therein. A longitudinally compressible member is disposed within the first bore such that a first end portion of the compressible member is operatively coupled to the tubular first portion. The compressible member includes a second free end portion opposite the first end portion and a second bore defined therein from the first end portion to the second end portion. A substantially tubular second portion is coupled to the first end portion of the tubular first portion. Thus, this embodiment eliminates the need for the protrusion coupled to the wall of the first portion of the adapter.

Upon assembly of either embodiment of the airway adapter with a tubular adapter by means of longitudinal movement of the two components toward one another, the end of the compressible member extending beyond the axial protrusion contacts an end wall of the tubular adapter. Further movement of the airway adapter toward the tubular adapter compresses compressible member in a longitudinally direction to effect a resilient seal with the tubular adapter. In this configuration, the bore in the compressible member is in communication with the passage of the tubular adapter.

Through use of the present invention, deadspace in the breathing circuit, and specifically within the airway adapter, is greatly reduced. Further, as the compression of the resilient sleeve does not cause a substantial effective variation in the internal radial or lateral dimensions of the airway passage between the tubular adapter and the sampling bore, a substantially smooth flow of gases through the airway adapted is facilitated while also minimizing any unswept volumes within the airway adapter.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE PRESENTLY PREFERRED EMBODIMENTS OF THE INVENTION

Figure 1:
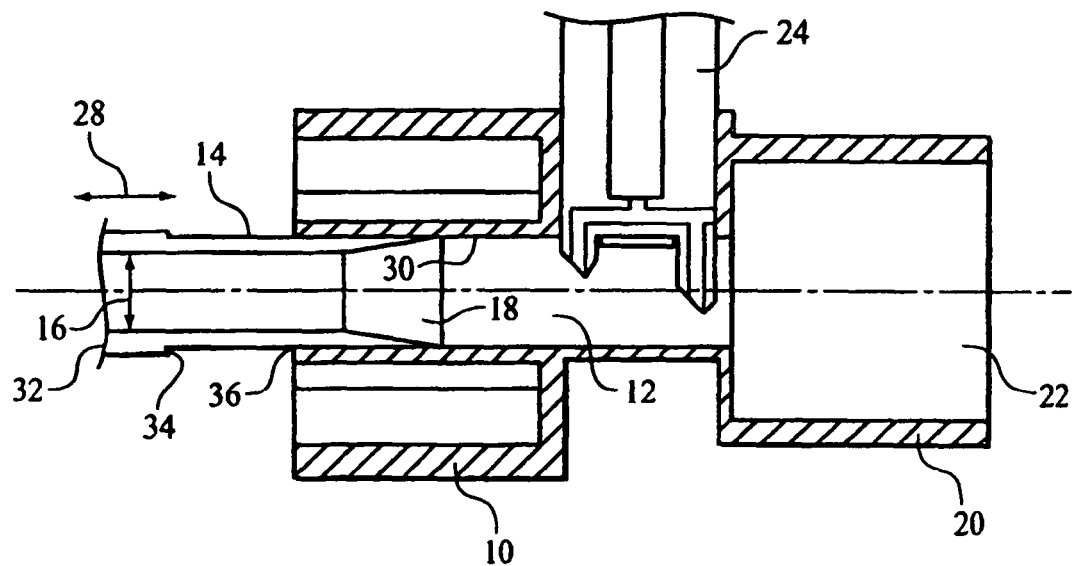
FIG. 1 is a cross-sectional view of one embodiment of a conventional airway adapter.
Figure 2:
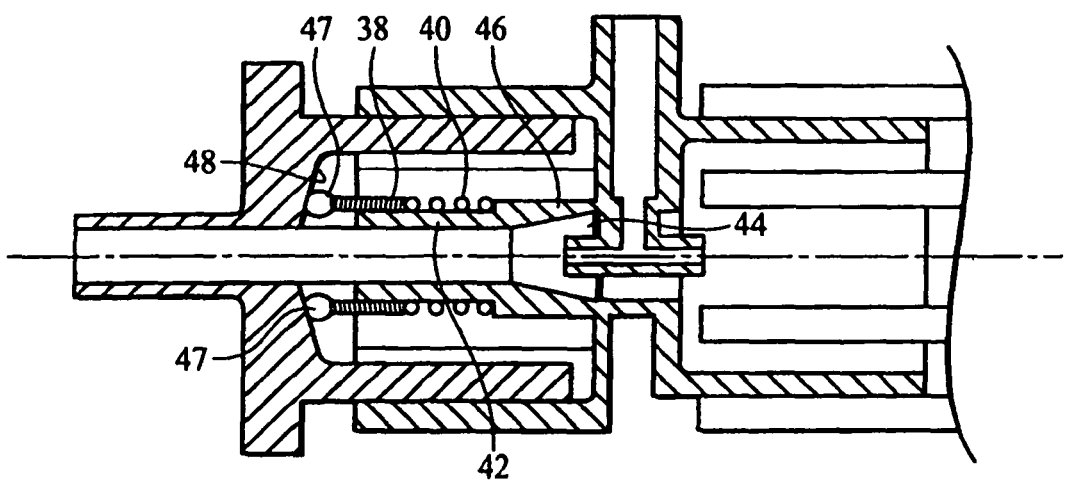
FIG. 2 is a cross-sectional view of a second embodiment of a conventional airway adapter.

One embodiment of the present invention provides an airway adapter suitable for use with patients having low tidal volumes, e.g., neonates, which minimizes deadspace in the airway and promotes substantially smooth flow of gases through the adapter while minimizing unswept volumes. Referring now to the drawings in general, and initially to FIGS. 3-6 in particular, an exemplary embodiment of an airway adapter according to the principles of the present invention is illustrated and denoted generally by reference numeral 50. The illustrated embodiment of airway adapter 50 is utilized to provide a releasable connection between a ventilation tube (not shown) and a tubular adapter, such as an endotracheal tube adapter 52.

Tubular adapter 52 comprises a substantially tubular portion 250 including an outer wall 252 having a bore 254 extending therethrough. An inner surface 256 of bore 254 extends to a shallow frustoconical end wall 258 into which an axial passage 260 opens. The exterior of outer wall 252 comprises a tapered outer surface 262 having a diameter that increases as the distance from outer end 259 increases and terminates at a transversely extending flange 264. On the longitudinally opposite side of flange 264 from outer wall 252, axial passage 260 extends through a tubing adapter protrusion 266, which is sized to receive a tubing, such as an endotracheal tube, extending to the patient. Gases received from the endotracheal tube (not shown), which frictionally engages over tubing adapter protrusion 266, enters axial passage 260. Neonatal and infant endotracheal tubes generally have diameters less than 4 mm. Thus, the present invention contemplates sizing tubing adapter protrusion 266 so as to receive the ends of even these relatively small sized endotracheal tubes.

Airway adapter 50 includes a first portion 54 for releasably engaging the endotracheal tube adapter 52, a second portion (or ventilation tube connector portion) 56 for releasably engaging a ventilation tube (not shown) and a sampling portion 58 disposed intermediate the first and second portions 54 and 56. A sample of expired gases from a patient flowing through the airway adapter is drawn from sampling portion 58.

Second portion 56 of airway adapter 50 is substantially tubular and includes an outer wall 60 having a tapered internal bore 61 defined by an inner surface 62 and an outer surface 64. The taper in the inner surface of the internal bore is oriented such that the diameter of the bore decreases as the distance from an second end 63 thereof increases. Second portion 56 also includes a taper in outer surface 64, which is oriented such that the diameter of outer surface 64 increases diameter as the distance from second end 63 increases. This exterior taper facilitates connection the second portion with ventilation tube of various manufactures.

Sampling portion 58 includes a sample tap structure 66 having a sample port 68 extending from the exterior of airway adapter 50 to an interior location proximate a central axis of the airway adapter. More specifically, sample port 68 includes an outer bore 70 of relatively larger diameter for receiving a sampling tube (not shown) therein such that the sampling tube extends into port 68. Sample port 68 also includes a coaxial inner bore 72 extending from outer bore 70 and opening into an axially extending sampling bore 74 within the adapter. In the exemplary embodiment shown in FIGS. 3-6, sample port 68 minimizes the condensation of moisture and other contaminants from the patient's breath, because of its unique configuration in which the end of the port protrudes slightly into sampling bore 74.

Airway adapter 50 further includes a barrier wall 80 extending transversely across the interior thereof and penetrated only by axially extending sampling bore 74.

First portion 54 of airway adapter 50 is substantially tubular and includes an outer wall 82 having a tapered internal bore 83 defined by an inner surface 84 thereof. The diameter of this bore in first portion 54 decreases as a distance from an outer first end 85 increases. The exterior surface of first portion 54 of airway adapter 50 comprises a substantially cylindrical outer surface 86. The taper of inner surface 84 facilitates frictional engagement with tapered outer surface 262 of tubular adapter 52 when the airway adapter is connected to tubular adapter 52, as discussed in more detail below.

First portion 54 further includes an axial protrusion 88 extending from barrier wall 80 and having a bore 90 defined therethrough. Bore 90 is in fluid communication with sampling bore 74. The present invention contemplates tapering bore 90 such that the diameter of the bore decreases in a direction toward sampling bore 74. It is to be understood that such tapering can be eliminated. An outer surface 92 of protrusion 88 is also tapered such that the outer diameter of the protrusion increases in a direction toward barrier wall 80.

A longitudinally compressible member in the form of a resilient sleeve 100 is secured over axial protrusion 88 such that a portion of the sleeve extends beyond the end of the protrusion. Resilient sleeve 100 includes a first skirt 102, having a bore 104 sized to resiliently fit over axial protrusion 88 and grip outer surface 92 thereof. First skirt 102 necks down at an annular transition 106, which defines a transition bore 108 of like diameter to the outer end of bore 90. A bulbous or teardrop-shaped compression segment 110 having bore 111 defined therein extends axially from annular transition 106 and comprises an outwardly flaring frustoconical portion 112 terminating at a partial spherically-shaped portion 114 through which exit bore 116, of like diameter to transition bore 108, extends. A second skirt 118 extends axially from compression segment 110 and defines a cap bore 120. The present invention contemplates that resilient sleeve 100 is molded from a suitable elastomer, such as silicone rubber or blow-molded polyethylene.

Figure 3:
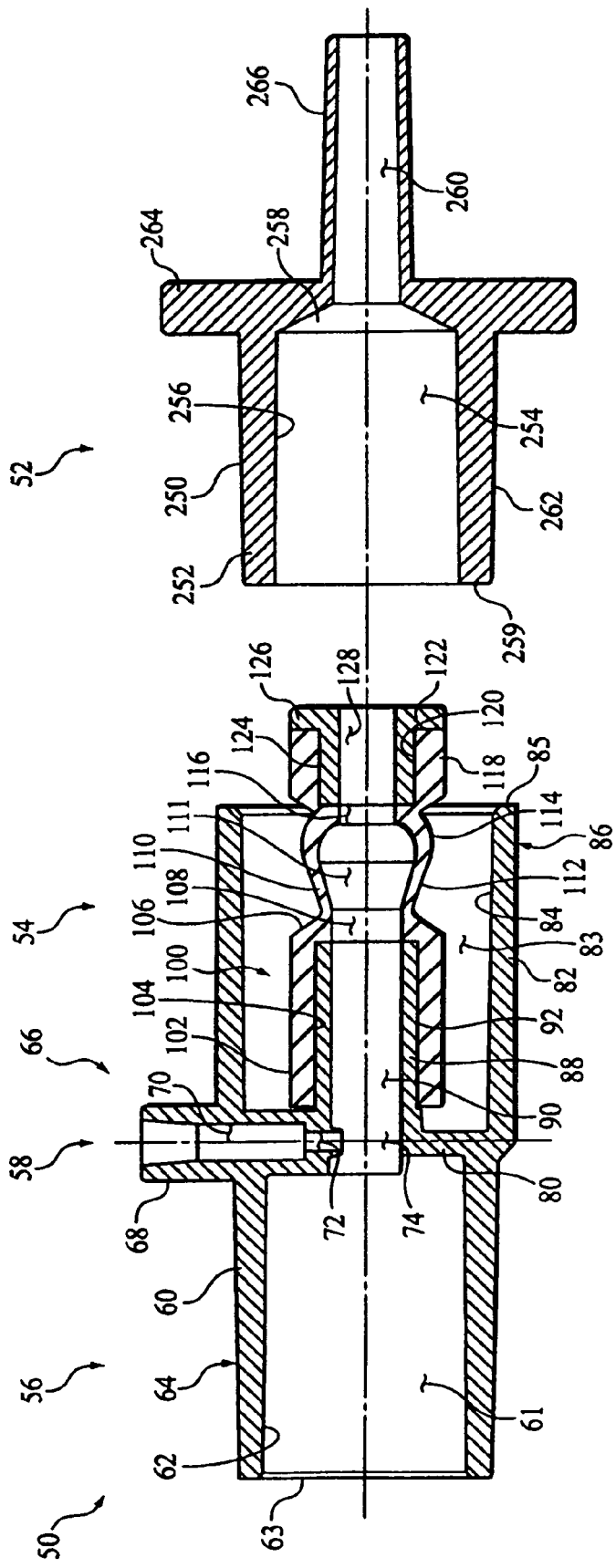
FIG. 3 is an exploded sectional view of a first embodiment of an airway adapter according to the principles of the present invention illustrating a resilient sleeve in an extended position prior to assembly with a tubular adapter.
Figure 4:
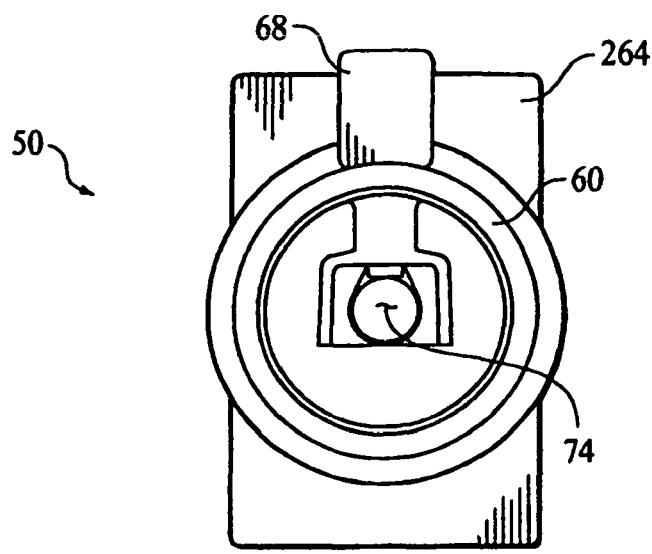
FIG. 4 is an end view of the airway adapter of FIG. 3.

An end cap 122 is provided at the end of resilient sleeve 100. End cap 122 includes a substantially cylindrical barrel 124 and a flange 126 extending transversely therefrom. An axial bore 128 extends through the barrel and the flange. Barrel 124 is received within a cap bore 120 of second skirt 118 such that flange 126 abuts the end of the second skirt. Axial bore 128 of end cap 122 has a diameter that is substantially the same as exit bore 116 and that is coaxially aligned therewith. The present invention contemplates forming end cap 122 from any material suitable for use in this operating environment, such as thermoplastic acrylic. As depicted in FIG. 3, end cap 122 may protrude substantially longitudinally beyond the outer end of first portion 54 of airway adapter 50. End cap 122 provides structural support for the distal tip of the resilient sleeve, which contacts the tubular adapter, to prevent the tip of the sleeve from collapsing in on itself when contacting the tubular adapter. End cap 122 also all an even force to be transmitted on the perimeter of the sleeve. The present invention contemplates coupling end cap 122 and sleeve 100 using any conventional technique. For example, these two items can be provided as separate component that are assembled during the manufacturing process, or they can be insert molded.

As previously described, due to the wide manufacturing tolerances in the plastic parts from which outer wall 82 of first portion 54 of airway adapter 50 and outer wall 252 of tubular adapter 52 are formed, the airway adapter and the tubular adapter may have a fairly wide variation in the longitudinal travel over which they may be pushed toward one another before a tight-fitting relationship therebetween is established. The lesser the distance that they must be pushed toward one another to form a tight fit, the greater the deadspace potentially created in the airway. As previously discussed, this deadspace is undesirable, particularly in low tidal volume applications.

Figure 5:
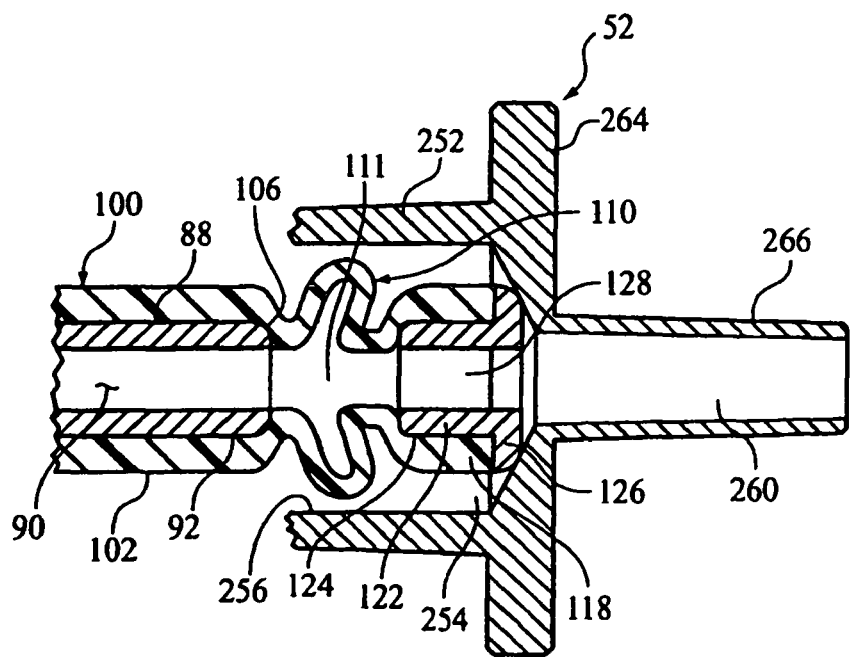
FIG. 5 is a side view of a portion of the airway adapter and tubular adapter of FIG. 3 showing the resilient sleeve in a relatively compressed position after contact with an internal end wall of the tubular adapter.
Figure 6:
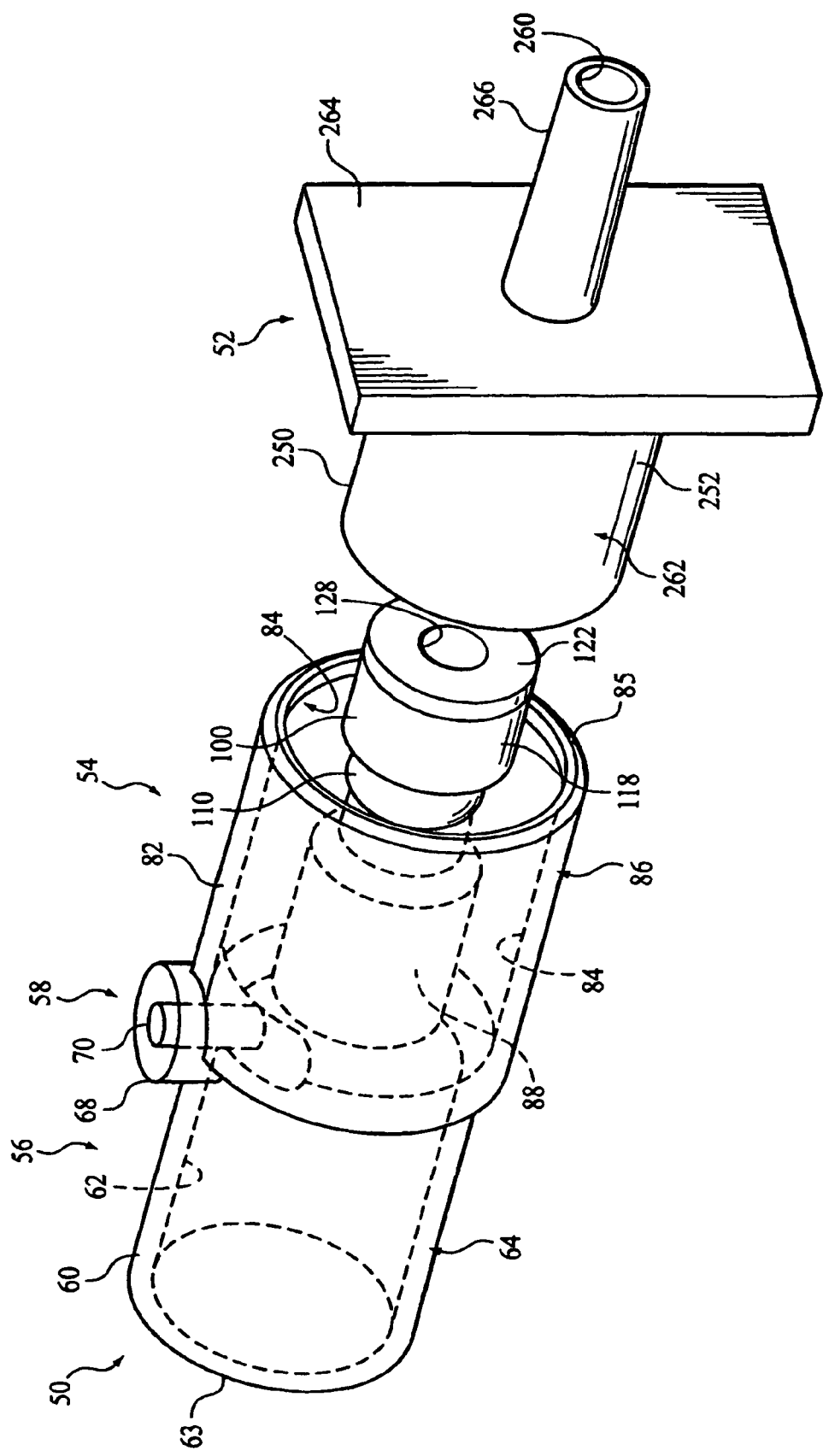
FIG. 6 is an exploded perspective view of the airway adapter and tubular adapter of FIG. 3.

The present invention minimizes deadspace when airway adapter 50 and tubular adapter 52 are longitudinally joined by use of resilient sleeve 100. Prior to assembly, resilient sleeve 100 is in an extended position as shown in FIG. 3. When airway adapter 50 and tubular adapter 52 are pushed toward one another upon assembly, outer wall 252 of tubular adapter 52 is fitted inside of outer wall 82 of first portion 54 of airway adapter 50. As airway adapter 50 and tubular adapter 52 are pushed further toward one another, flange 126 of end cap 122 engages frustoconical end wall 258 within bore 254 of tubular adapter 52 and forms a seal therewith, as shown in FIG. 5. Because of the radial dimension of the end cap flange 126, in combination with the shallow angle of frustoconical end wall 258 to a perpendicular to the longitudinal axes of airway adapter 50 and tubular adapter 52 in combination, when the seal is formed therebetween, substantially all of the gas received through the axial passage 260 of tubular adapter 52 is constrained to flow through end cap bore 128, exit bore 116, compression segment bore 111, transition bore 108, and into bore 90 of axial protrusion 88 to sampling bore 70. Thus, deadspace is minimized.

Typically, at the time flange 126 of end cap 122 is first in contact and sealingly engages frustoconical end wall 258, the fit between tubular adapter 52 and airway adapter 50 is not a tight fit. Instead, the two components must be pushed further toward one another to ensure a suitably tight, frictional, interference (press-fit) connection. As airway adapter 50 and tubular adapter 52 are pushed longitudinally further toward one another, the force acting on inner resilient sleeve 100 causes compression segment 110 to foreshorten longitudinally and to collapse within itself to a greater or lesser extent, depending on the longitudinal travel required to ensure the aforementioned tight, interference (press-fit) connection. This causes the compression segment 110 to take on substantially the configuration illustrated in FIG. 5, while maintaining a resilient longitudinal bias to maintain the seal between flange 126 and frustoconical end wall 258.

In this manner, a substantial portion of the deadspace, which would otherwise be present in the airway, is essentially removed from the interior of first portion 54 of airway adapter 50. Further, because there is not a substantial or protracted change in the bore diameters through which the expired gases flow from the patient, a smooth flow of gases to sampling bore 70 is achieved.

Figure 7:
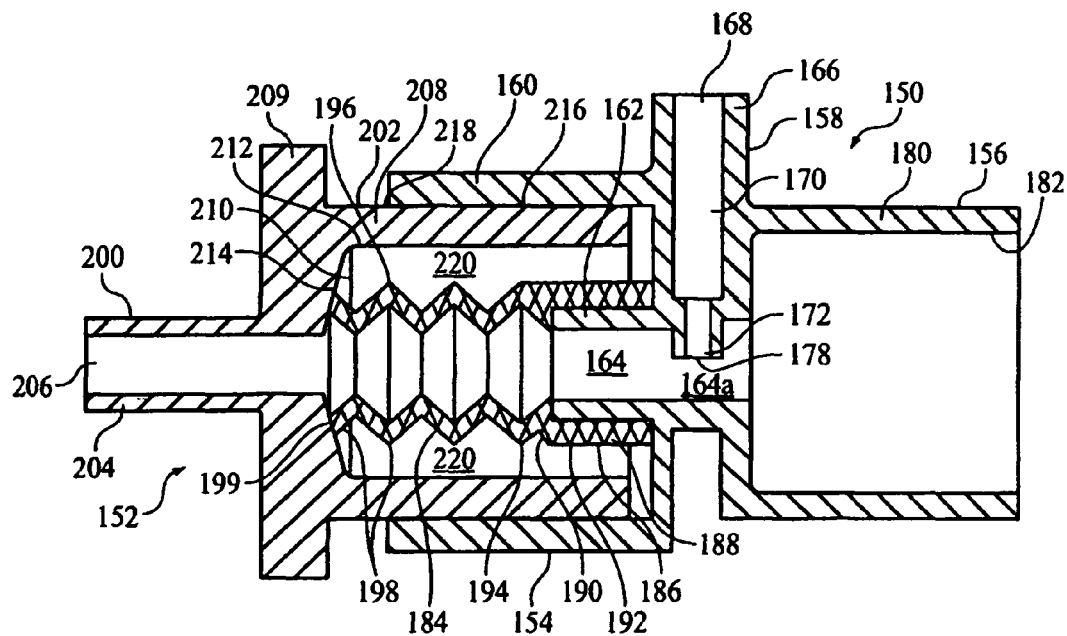
FIG. 7 is cross-sectional view of a second embodiment of an airway adapter according to the principles of the present invention

Referring now to FIG. 7, a second exemplary embodiment of an airway adapter according to the present invention is illustrated and denoted generally by reference numeral 150. Airway adapter 150 is utilized to provide a releasable connection between a ventilation tube (not shown) and a tubular adapter such as an endotracheal tube adapter 152, which is configured similar to tubular adapter 52. Airway adapter 150 includes a first portion 154 for releasably engaging tubular adapter 152, a second portion (or ventilation tube connector portion) 156 for releasably engaging a ventilation tube (not shown) and a sampling portion 158 through which a sample of the gases flowing through the airway adapter may be drawn for analysis.

First portion 154 is substantially tubular and includes an outer wall 160 that is slightly tapered in diameter on its inner surface to promote releasable engagement with tubular adapter 152 upon assembly therewith. First portion 154 further includes an axial protrusion 162 positioned closer to a center of the airway adapter than outer wall 160. Axial protrusion 162 originates from approximately the same point along the longitudinal length of airway adapter 150 as outer wall 160 and extends in the same longitudinal direction. However, outer wall 160 extends distally longitudinally further from the point of origin than axial protrusion 162. Stated differently, outer wall 160 is longer than axial protrusion 162, the longitudinal length of axial protrusion 162 being approximately one-third to one-half as long as outer wall 160.

Both axial protrusion 162 and outer wall 160 originate at a location along the longitudinal length of the airway adapter 150 where a sample tap structure 166 of sampling portion 158 of airway adapter 150 is located. It will be understood and appreciated by those skilled in the art that axial passage 162 and outer wall 160 of first portion 154 may be separately formed and sealingly engaged with sample tap structure 166 of sampling portion 158 or may be integrally formed therewith. Each such variation is contemplated to be within the scope of the present invention.

Sample tap structure 166 of sampling portion 158 is substantially tubular in shape and includes sample port 168 extending therethrough transversely to the longitudinal axis of airway adapter 150. Sample port 168 includes an outer bore 170 of relatively larger diameter for receiving a sampling tube therein and a coaxial inner bore 172 extending from outer bore 170 and opening into sample bore 164a, which is in communication with bore 164 of axial protrusion 162.

Sampling portion 158 of airway adapter 150 extends downwardly to approximately the center of thereof. In this way, any contaminants or other constituents that may collect in bores 164 and 164a are prevented from entering sample port 168 through open end 178 thereof. Gases passing through bore 164a may be drawn through sample port 168 and transported to a remote location for analysis.

Second portion 156 of airway adapter 150 is substantially tubular and includes an outer wall 180 having a bore defined by an inner surface 182. The internal bore diameter of second portion 156 substantially approximates the outer diameter of a suitable ventilation tube (not shown) with which airway adapter 150 may be utilized. Inner surface 182 of outer wall 180 of second portion 156 is slightly tapered to facilitate releasable engagement with such ventilation tube (not shown).

Airway adapter 150 further includes a compressible member in the form of resilient sleeve 184. Resilient sleeve 184 is located between outer wall 160 of and axial protrusion 162 of first portion 154. Resilient sleeve 184 includes a longitudinally inner portion 186 having a substantially tubular skirt 188 terminating at annular lip 190. Tubular skirt 188 envelopes and sealingly engages an outer surface 192 of axial protrusion 162 of first portion 154, while annular lip 190 abuts terminal end 194 of axial protrusion 162. Tubular skirt 188 is of a longitudinal length that is less than or equal to the longitudinal length of axial protrusion 162.

Resilient sleeve 184 further includes a longitudinally outer portion 196 including a plurality of accordion-like pleats or corrugations 198. These accordion-like pleats permit resilient sleeve 184 to accommodate a variable longitudinal dimension within the framework of the assembly of rigid molded plastic parts that make up the remainder of airway adapter 150 and complementary tubular adapter 152, as more fully described below. Longitudinally outer portion 196 of resilient sleeve 184 terminates in an end portion 199 which is located distally from tubular skirt 188.

A typical endotracheal tube adapter 152, complementary to airway adapter 150, and which may be used therewith in the present invention, includes an endotracheal tube receiving section 200 and an adapter section 202. Endotracheal tube receiving section 200 is tubular and includes a wall 204 defining an axial passage 206 therethrough. Gases received from the endotracheal tube (not shown) enters the airway adapter through central conduit 206. Upon assembly, the endotracheal tube (not shown) is fitted over the end of wall 204. The perimeter of tubular wall 204 is sized so as to receive endotracheal tubes of the relatively small sizes often used by neonates.

Adapter section 202 of endotracheal tube adapter 152 is tubular and includes an outer wall 208 surrounding a central bore 210 defined by a substantially cylindrical inner surface 212 of outer wall 208. Inner surface 212 terminates at frustoconical end wall 214, which leads to the perimeter of axial passage 206.

Outer surface 218 of outer wall 208 of adapter section 202 of endotracheal tube adapter 152 is slightly tapered, decreasing in diameter from a location near flange 209 toward the opposite end of outer wall 208 to promote releasable, frictional engagement with the interior of outer wall 160 of first portion 154 of airway adapter 150 upon assembly therewith.

When assembled, tapered inner surface 216 of outer wall 160 of sampling airway adapter 150 releasably engages tapered outer surface 218 of tubular wall 208 of tubular adapter 152. Tubular adapter 152 and airway adapter 150 are fitted together into a tight-fitting, interference relationship.

The embodiment of FIG. 7 minimizes deadspace, particularly in region 220, by use of resilient sleeve 184. Prior to assembly of airway adapter 150 with tubular adapter 152, resilient sleeve 184 is in an extended position (not shown). That is, accordion-like pleats 198 of second end portion 196 of compressible member 184 are in an extended position such that the pleats are more relaxed and of lesser radial extent. When airway adapter 150 and tubular adapter 152 are pushed longitudinally toward one another, end portion 199 of second end portion 196 of compressible member 184 contacts frustoconical end wall 214 of tubular adapter 152 as shown. To achieve this result, it will be understood that the longitudinally outer portion 196 of resilient sleeve 184 is of a length which, when extended, is sufficient to contact tapered portion 214 no matter how large or small the distance which airway adapter 150 and tubular adapter 152 must be pushed toward one another to mutually and securely engage. It is, therefore, desirable that the extended longitudinal length of longitudinally outer portion 196 of resilient sleeve 184 extend beyond longitudinal length of outer wall 160 of airway adapter 150.

As airway adapter 150 and tubular adapter 152 are pushed toward one another, pressure on resilient sleeve 184 exerted through frustoconical end wall 214 causes the pleated, longitudinally outer portion 196 to contract, while maintaining contact between end portion 199 thereof and frustoconical end wall 214. This causes pleats 198 of longitudinally outer portion 196 of resilient sleeve 184 to become longitudinally closer together and the radially outer ends to extend more radially outward to the configuration illustrated in FIG. 7. However, resilient sleeve 184 provides enough resilient bias responsive to the pressure placed on it that the contact between end portion 199 thereof and frustoconical end wall 214 provides a substantially gas-tight and fluid-tight seal. Thus, gases that enter bore 164 from axial passage 206 are substantially prevented from entering region 220 and are, instead, maintained in the bore 164.

Thus, it can be appreciated that the present invention minimizes the deadspace present in the breathing circuit by substantially blocking off those regions 220 where deadspace tends to be located from bore 164. Further, because accordion-like pleats 198 do not cause a substantial variation in the perimeter of bore 164, a generally smooth flow of gases therethrough is facilitated while also minimizing the unswept volumes in the gas flow path.

Figure 8:
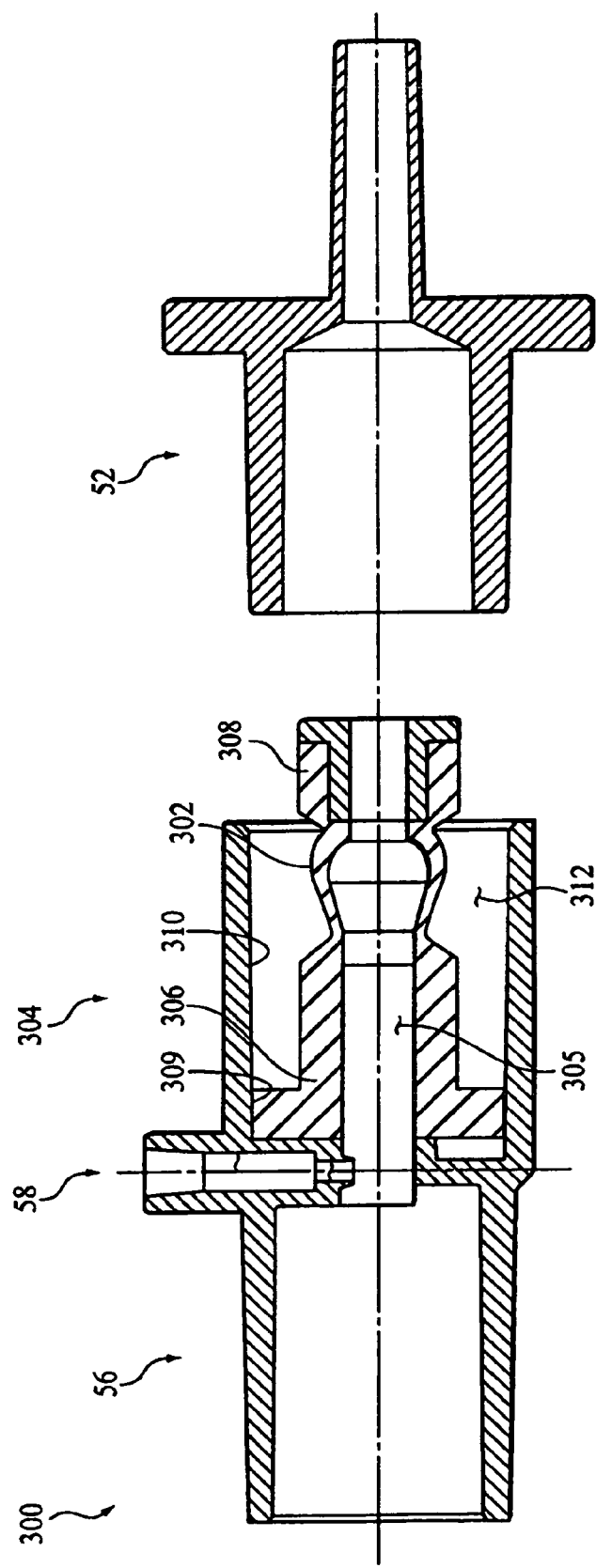
FIG. 8 is an exploded sectional view of a third embodiment of an airway adapter according to the principles of the present invention.

FIG. 8 illustrates a third embodiment of a airway adapter 300 according to the principles of the present invention. It can be appreciated that this embodiment is structurally similar to that shown in FIGS. 3-6, except for the manner in which a compressible member 302 is attached to a tubular first portion 304 of adapter 300. In this embodiment, a first end portion 306 of compressible member 302 is operatively coupled within first portion 304. As in the previous embodiment, a bore 305 is defined in the compressible member from first end portion 306 to and a second free end portion 308.

In the illustrated exemplary embodiment of the invention, first end portion 306 of compressible member 302 includes a flange 309 disposed at the first end portion about its periphery. Flange 309 frictionally engages a wall 310 of a bore 312 to maintain the compressible member in place within first portion 304 of the adapter. It is to be understood that other techniques and configurations for attaching the compressible member to the first portion are contemplated by the present invention. For example, instead of forming flange 308 integrally with first end portion 306 of compressible member 302, the flange can be separate from the compressible member. In this configuration, the flange serves as a separate friction fitting element that is disposed between the first end portion of the compressible member and the wall of the bore so as to maintain the compressible member in place within the bore. Of course, the flange or other fitting element for attaching the compressible member to the first portion of the adapter can have a variety of configurations, shapes, and sizes and can include multiple parts.

It will be understood and appreciated by those of ordinary skill in the art that variations on the compressible member may be made which fall within the scope of the invention. For instance, rather than comprising an accordion-pleated resilient sleeve, the compressible member of the present invention may comprise a pliable but solid, tubular structure so that buckling is avoided. Such variations are contemplated to be within the scope of the present invention.

Figure 10:
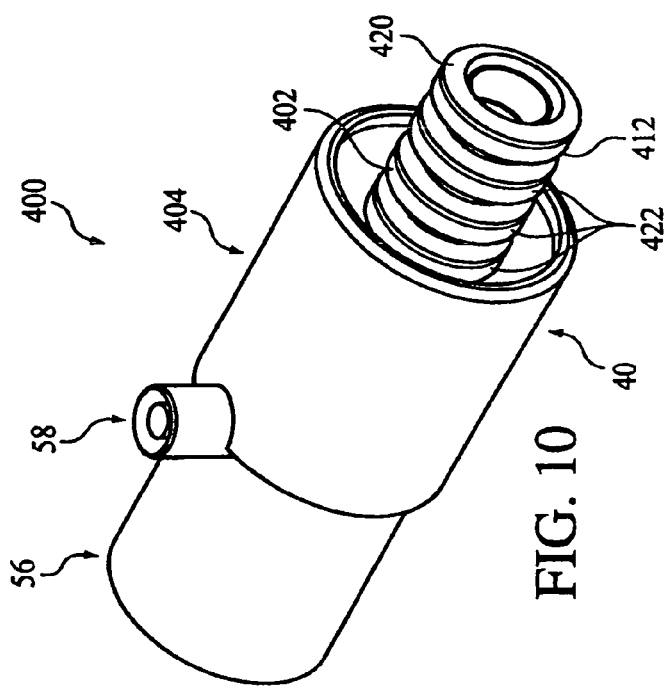
FIGS. 9 and 10 are top and perspective views, respectively, of a fourth embodiment of an airway adapter according to the principles of the present invention.
Figure 9:
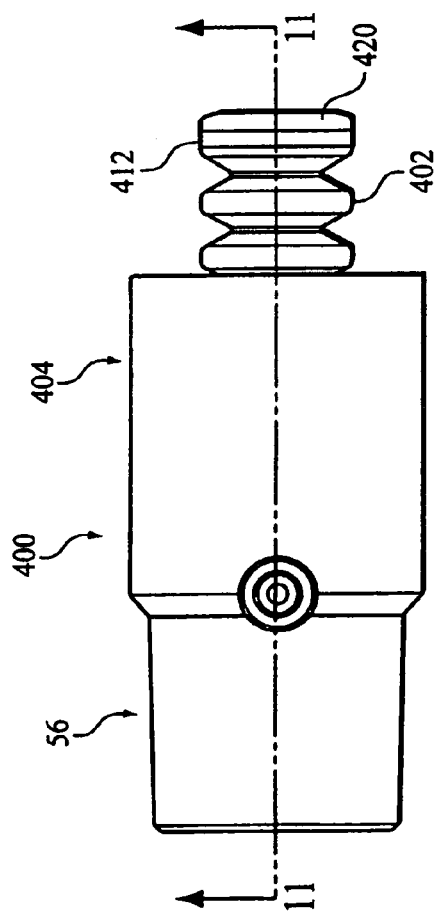
Figure 11:
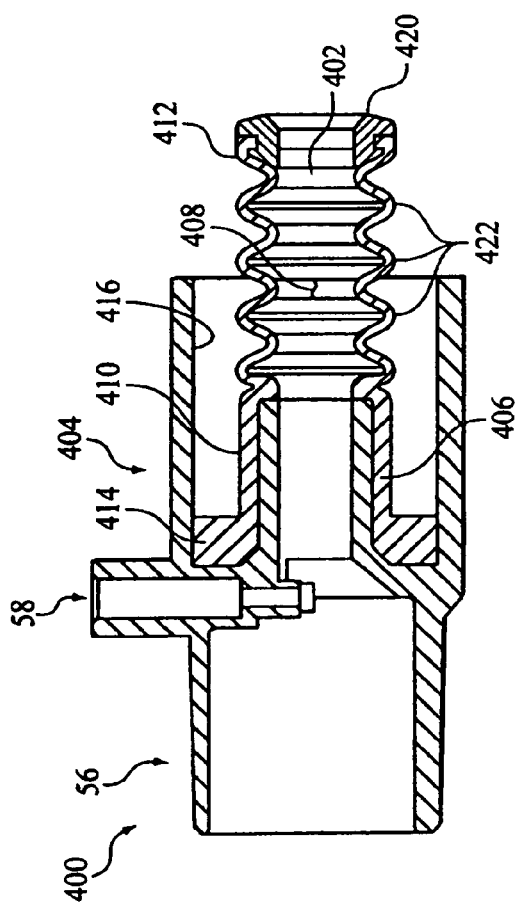
FIG. 11 is cross-sectional view of the airway adapter of FIGS. 9 and 10 taken along line 11-11 of FIG. 9.

FIGS. 9-11 illustrate a fourth embodiment of a airway adapter 400 according to the principles of the present invention. It can be appreciated that this embodiment is structurally similar to that shown in FIGS. 3-6, except for the structure for compressible member 402, which is somewhat similar to that shown in FIG. 7. In the illustrated embodiment, compressible member 402 is attached to a tubular first portion 404 of adapter 400 via a protrusion 406. However, the present invention contemplates attaching compressible member 402 to tubular first portion 404 as shown in FIG. 8. As in the previous embodiments, a bore 408 is defined in the compressible member from first end portion 410 to and a second free end portion 412. Bore 408, in the illustrated embodiment, has an effective flow path diameter that is substantially equal to a bore defined in protrusion 406.

In the illustrated exemplary embodiment of the invention, first end portion 410 of compressible member 402 is disposed around, and in frictional engagement with protrusion 406. End portion 410 also includes a flange 414 disposed about the periphery of the compressible member. Flange 414, like flange 308 in the previous embodiment, frictionally engages a wall of a bore 416 to maintain the compressible member in place within the adapter. It is to be understood that other techniques and configurations for attaching the compressible member to the first portion are contemplated by the present invention. For example, instead of forming flange 414 integrally with first end portion 410 of compressible member 402, the flange can be separate from the compressible member.

Compressible member 402 preferably includes an end cap 420 that is attached to end portion 412 in any suitable manner, including the techniques discussed above. In this embodiment, a groove is defined in a periphery of the cap that receives a tongue or protrusion at end portion 412 to retain the end cap on the compressible member. It should be noted that end cap 420 is optional and, if provided, can have a variety of shapes, sizes, and configurations.

Portion 412 of compressible member 402 includes a plurality of pleats or gussets 422, so that end free end portion of the compressible member collapses in an accordion-like matter when a force is applied to end cap 420. That is, when forced against the interior end wall of an endotracheal adapter, the pleats of the accordion-like wall structure compress in the longitudinal direction, foreshortening end portion 412 of compressible member 402.

The pleated portion of compressible member 402 is structured such that when no force is acting on the free end, the compressible member moves to an undeflected position as generally shown in FIGS. 9-12. This configuration for compressible member provides a bias force that is sufficient to maintain a contact between end cap 412 and end wall of a tubular adapter 52. In addition, when pulled back from the interior end wall of an endotracheal adapter, the elastic nature of the pleated portion 412 of compressible member 302, and, specifically, the accordion-like wall structure thereof, causes the accordion-like to expand again in the longitudinal direction. In this manner, the compressible member adjusts in length to abut against the interior end wall of the endotracheal adapter to accommodate the wide variety of potential distances between the adapters when they are joined due, for example, to the manufacturing tolerances of these molded plastic components.

The advantages of a using a plurality of pleats is that is allows for a relatively high degree of control in the collapsibility of the compressible member so that the collapsing force is properly set and the manner in which the compressible member collapses is consistent and uniform. In addition, the relatively small area between the pleats when the compressible member is collapses helps minimize the unswept volume within the adapter and promotes a good flow of gas through the adapter.

It is to be understood that the number, size, shape, spacing, length, width, and other features of the pleats are subject to variation. The present invention is not intended to be limited to the specific configuration shown in FIGS. 9-11. In addition, compressible member 402 can be formed from any one of a variety of materials suitable for use in the present medical application.

In the embodiments discussed above, the airway adapter is considered to be a sampling airway adapter because it is structured to allow a portion of the gas passing through the adapter to be diverted to a sampling site. It should understood that the features of the present invention, such as the various embodiments for the compressible member or resilient sleeve, are equally applicable to other types of airway adapters. Thus, the term "airway adapter" or "adapter", as used herein, is intended to encompass all types of adapters used to join two components in a patient circuit (also referred to as ventilator circuit). Airway adapters suitable for use in the present invention include, but are not limited to, the following:

1) sampling airway adapters that divert gas from a patient circuit;
2) mainstream gas measurement airway adapters that allow gas to be measured in the patient circuit. See, e.g., U.S. Pat. No. 5,693,944.
3) Y-adapters (Y-piece adapters) that couple an inspiratory limb and an expiratory limb to endotracheal or tracheal tube;
4) T-adapters (T-piece adapters) that connect external components to a ventilator circuit;
5) size adapters that step-up or step-down the diameter of the patient circuit; and
6) sensor adapters that provide an attachment point for a sensor, such as a flow sensor, pressure sensor, or temperature sensor, to the patient circuit.

Figure 12:
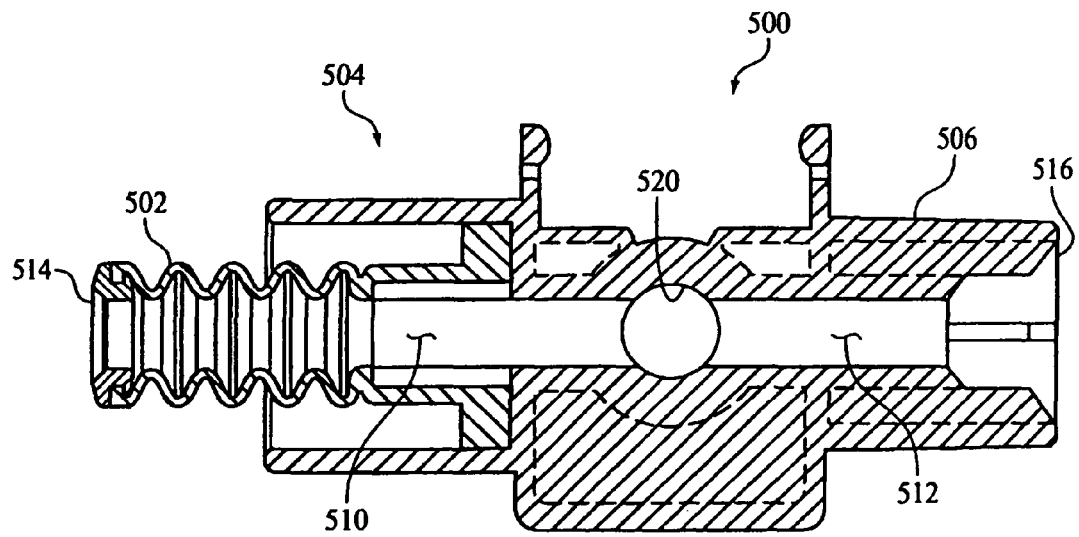
FIG. 12 is a cross-sectional view of fifth embodiment of an airway adapter according to the principles of the present invention.

FIG. 12 illustrates and exemplary embodiment of a mainstream gas measurement adapter 500 that provides an attachment point for a gas measurement device (not shown) in a patient circuit. Such an airway adapter is typically used to measure the carbon dioxide ($CO_2$) or oxygen ($O_2$) concentration in the gas passing through the adapter without diverting the gas to a sampling site. Gas measurement adapter 500 includes a compressible member 502 attached to a tubular first portion 504 of adapter housing 506. Compressible member 502 is functionally and structurally similar to compressible member 402 in the previous embodiment, except that compressible member 502 does not fit over a protrusion formed in adapter housing 506. Instead, compressible member 502 attaches to housing 506 in the same manner compressible member 302 attaches to tubular portion 304 in FIG. 8. A first bore 510 is defined in compressible member 502 and a second bore 512 is defined in adapter housing 506 so that gas readily flows between a first end portion 514 to a second end portion 516 of the airway adapter.

Measurement of the constituents of the gas passing through bore 512 is made possible by providing an aperture 520 in housing 506. Aperture 520, which is sealed by a window, allows the gassing in front of the aperture to be irradiated, so that the gas contents can be measured using conventional gas measurement techniques. This embodiment of an airway adapters is provided to allow those skilled in the art to understand how the compressible member, and other components, of the present invention can be used in conjunction with other types of airway adapters in addition to the sampling airway adapters shown in FIGS. 3-11. Of course, depending on the type of airway adapter used, modifications in the compressible member may be necessary.

Figure 13:
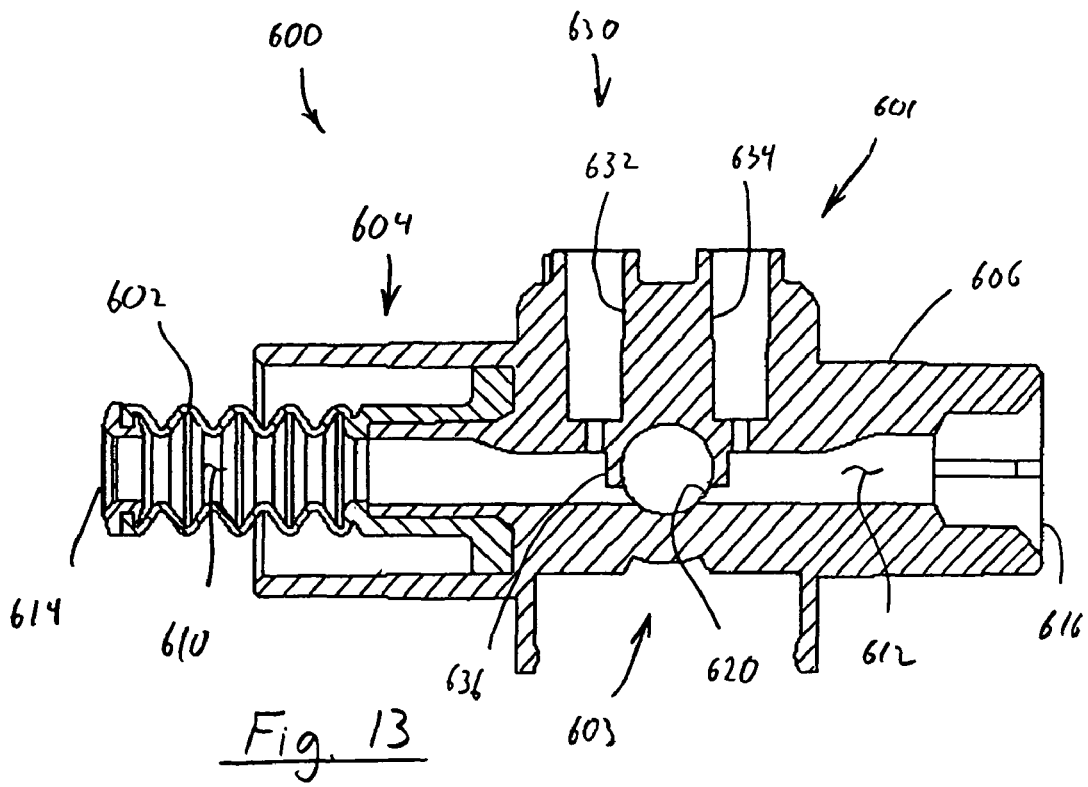
FIG. 13 is a cross-sectional view of sixth embodiment of an airway adapter according to the principles of the present invention.

FIG. 13 is a cross-sectional view of sixth embodiment of an airway adapter 600 according to the principles of the present invention. Airway adapter 600 provides both a flow measuring capability via a flow measuring assembly, generally indicated at 601, and a mainstream gas monitoring capability via a gas constituent monitoring assembly, generally indicated at 603. Airway adapter 600 includes a compressible member 602 attached to a tubular first portion 604 of adapter housing 606. Compressible member 602 is functionally and structurally similar to compressible member 502 in the previous embodiment. As in the previous embodiment, a first bore 610 is defined in compressible member 602 and a second bore 612 is defined in adapter housing 606 so that gas readily flows between a first end portion 614 to a second end portion 616 of the airway adapter.

Measurement of the constituents of the gas passing through bore 612 is made possible by providing an aperture 620 in housing 506. Aperture 620, which is sealed by a window, allows the gas in front of the aperture to be irradiated, so that the gas contents can be measured using conventional gas measurement techniques. A second aperture, generally opposite the first aperture (also sealed with a window), can also be provided. When two apertures are used, light or other energy is transmitted from a source (not shown) to a detector (also not shown), along an optical path that generally traverses bore 612 and passes through both apertures. It is to be understood that aperture 620 can have a variety of configurations and can include other structures, such as luminescent material and/or heaters as known in the art.

Flow measuring assembly 601 is provided in a second portion 630 of housing 606 to measure the flow of gas passing through bore 612. Flow measuring assembly 601 in the illustrated exemplary embodiment includes a first aperture 632 and a second aperture 634 defined in a wall of the second portion. Each aperture is in fluid communication with bore 612. A flow element 636 is provided between the first aperture 632 and second aperture 634 so that a pressure drop is created between these two apertures. The flow of gas is measured or monitored using any conventional technique.

It is to be understood that the flow element can have a variety of configurations, including being a movable element, rather than the fixed configuration shown in FIG. 13. Also, apertures 632 and 634 can have other configuration. In the illustrated embodiment, a pressure sensor or mass flow sensor is coupled to each of these apertures to measure the flow.

Figure 14:
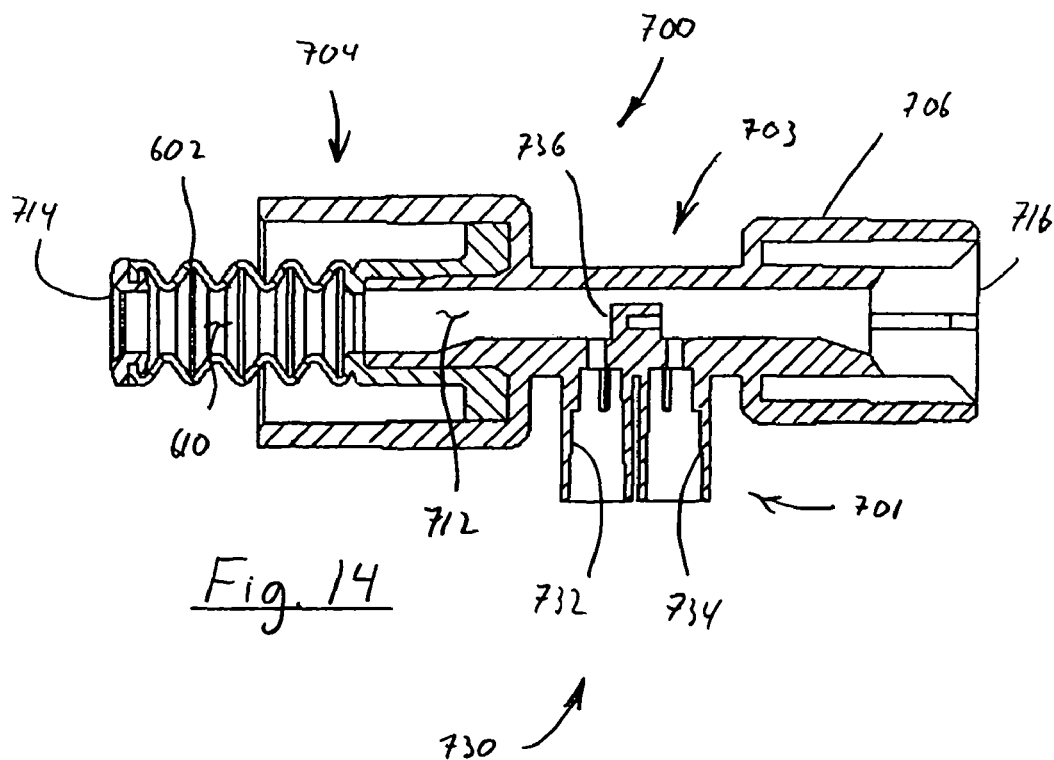
FIG. 14 is a cross-sectional view of seventh embodiment of an airway adapter according to the principles of the present invention.

FIG. 14 is a cross-sectional view of seventh embodiment of an airway adapter 700 according to the principles of the present invention. Airway adapter 700 provides a flow measuring capability via a flow measuring assembly, generally indicated at 701. In addition, an optional sidestream gas monitoring capability can be provided via a gas constituent monitoring assembly, generally indicated at 703. Airway adapter 700 includes a compressible member 602 attached to a tubular first portion 704 of adapter housing 706. As in the previous embodiment, a first bore 610 is defined in compressible member 602 and a second bore 712 is defined in adapter housing 706 so that gas readily flows between a first end portion 714 to a second end portion 716 of the airway adapter 700.

Flow measuring assembly 701 is provided in a second portion 730 of housing 706 to measure the flow of gas passing through bore 712. Flow measuring assembly 701 in the illustrated exemplary embodiment includes a first aperture 732 and a second aperture 734 defined in a wall of the second portion. Each aperture is in fluid communication with bore 712. A flow element 736 is provided between the first aperture 732 and second aperture 734 so that a pressure drop is created between these two apertures. The flow of gas is measured or monitored using any conventional technique.

As is the case with the previous embodiment, the flow element can have a variety of configurations, including being a movable element. Also, apertures 732 and 734 can have other configuration. A pressure sensor or mass flow sensor (not shown) is coupled to each of these apertures to measure the flow.

In the illustrated exemplary embodiment, the optional sidestream gas constituent monitoring capability provided by gas constituent monitoring assembly includes providing a passage or bore in flow element 736 so that gas can be drawn from bore 712 into a sidestream gas monitoring system (not shown). It is to be understood, that gas sampling port can be provided at other location in fluid communication with bore 712 in addition to or in place of that provided in flow element 736.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. An airway adapter structure comprising:
   a substantially tubular first portion comprising a wall having a proximal end, a first bore defined therein, and a protrusion having one end operatively coupled to the wall, having an open end, and having a second bore defined therethrough arranged to be axially aligned with the first bore;
   a longitudinally compressible member coupled to the protrusion and comprising coupling, transition, and compressible segments, the transition and compressible segments extend beyond the open end of the protrusion, and the transition segment connects the segments and includes an annular transition and a third bore defined therein in communication with the second bore, the second and third bores have same diameters;
   a substantially tubular second portion couplable to the proximal end of the substantially tubular first portion and comprising a fourth bore, wherein the second bore, the third bore, and the fourth bore are in fluid communication so as to define at least a portion of a gas flow path through the airway adapter; and a measuring assembly selected from at least one of a flow measuring assembly and a gas constituent monitoring assembly.

2. The airway adapter structure of claim 1, wherein the coupling segment is a first skirt portion disposed over the protrusion and coupled to the tubular first portion.

3. The airway adapter structure of claim 2, wherein the compressible segment is substantially teardrop shaped.

4. The airway adapter structure of claim 3, wherein the compressible member further comprises:
 a second skirt portion disposed on a longitudinally opposing side of the teardrop shaped segment from the first skirt portion, and
 an end cap having a barrel received within the second skirt portion, and an end cap bore defined in the barrel and in fluid communication with the third bore.

5. The airway adapter structure of claim 1, wherein the tubular first portion of the compressible member comprises at least one accordion-like pleat.

6. The airway adapter structure of claim 1, wherein the flow measuring assembly is provided in the second portion and comprises:
 (a) a first aperture defined in a wall of the second portion;
 (b) a second aperture defined in a wall of the second portion; and
 (c) a flow element disposed between the first aperture and the second aperture.

7. The airway adapter structure of claim 1, wherein the gas constituent monitoring assembly comprises:
 (a) a sampling portion having a fifth bore providing a passage between the second bore and fourth bore; and
 (b) a sample tap structure including a sampling port opening to the fifth bore and extending to an exterior of the airway adapter structure.

8. The airway adapter structure of claim 1, wherein the gas constituent monitoring assembly comprises:
 (a) a first aperture defined in a wall of the second portion; and
 (b) a first light transmissive window disposed in the first aperture.

9. The airway adapter structure of claim 8, wherein the gas constituent monitoring assembly further comprises:
 (c) a second aperture defined in a wall of the second portion generally opposite the first aperture; and
 (d) a second light transmissive window disposed in the second aperture.

10. An airway adapter structure comprising:
 a substantially tubular first portion comprising a wall having a first end part, a second end part, and a first bore defined therein, the first bore having a first bore diameter at a point separating the first and second end parts;
 a longitudinally compressible member disposed within the first bore and having a first end portion operatively coupled to the tubular first portion, a second end portion opposite the first end portion, and a transition portion having an annular transition and a second bore defined therein from the first end portion to the second end portion, wherein at a point of the coupling the second bore has the first bore diameter;
 (c) a substantially tubular second portion coupled to the first end part of the tubular first portion, wherein a third bore is defined in the tubular second portion, and wherein the second bore and the third bore are in fluid communication so as to define at least a portion of a gas flow path through the airway adapter; and
 (d) a measuring assembly selected from at least one of a flow measuring assembly and a gas constituent monitoring assembly.

11. The airway adapter of claim 10, wherein the compressible member includes a flange disposed at the first end portion, and wherein the flange and first bore at the first end portion of the tubular first portion are configured and arranged such that the flange frictionally engages a wall of the first bore to maintain the compressible member in place within the first bore.

12. The airway adapter of claim 10, wherein further comprising a friction fitting element disposed between the first end portion of the compressible member and a wall of the first bore so as to maintain the compressible member in place within the first bore.

13. The airway adapter structure of claim 10, wherein the compressible member comprises a resilient sleeve having a first skirt portion provided at the first end portion thereof.

14. The airway adapter structure of claim 10, wherein the second end portion of the compressible member comprises at least one accordion-like pleat.

15. The airway adapter structure of claim 10, wherein the flow measuring assembly is provided in the tubular second portion and comprises:
 (a) a first aperture defined in a wall of the second tubular portion;
 (b) a second aperture defined in a wall of the second tubular portion; and
 (c) a flow element disposed between the first aperture and the second aperture.

16. The airway adapter structure of claim 10, wherein the gas constituent monitoring assembly comprises:
 (a) a sampling portion having a fourth bore providing a passage between the second bore and the third bore; and
 (b) a sample tap structure including a sampling port opening to the fourth bore and extending to an exterior of the airway adapter structure.

17. The airway adapter structure of claim 10, wherein the gas constituent monitoring assembly comprises:
 (a) a first aperture defined in a wall of the tubular second portion; and
 (b) a first light transmissive window disposed in the first aperture.

18. The airway adapter structure of claim 17, wherein the gas constituent monitoring assembly further comprises:
 (c) a second aperture defined in a wall of the tubular second portion generally opposite the first aperture; and
 (d) a second light transmissive window disposed in the second aperture.

* * * * *